United States Patent [19]
Still et al.

[11] Patent Number: 5,420,805
[45] Date of Patent: May 30, 1995

[54] METHOD AND APPARATUS FOR DESIGNING MOLECULAR STRUCTURES USING AN ANALYTICAL SOLUTION FOR EFFECTIVE BORN RADII

[75] Inventors: William C. Still, New York, N.Y.; Frank P. Hollinger, North Haledon, N.J.

[73] Assignee: The Trustees of Columbia University in the City of New York, New York, N.Y.

[21] Appl. No.: 878,767

[22] Filed: May 5, 1992

[51] Int. Cl.$^6$ .......................... G06F 19/00; G09B 23/26
[52] U.S. Cl. ..................................... 364/578; 364/496; 364/497; 434/278
[58] Field of Search ............... 364/578, 496, 497, 499; 434/278, 279, 280

[56] References Cited

U.S. PATENT DOCUMENTS

| | | | |
|---|---|---|---|
| 4,855,931 | 8/1989 | Saunders | 364/499 |
| 5,025,388 | 6/1991 | Cramer, III et al. | 364/496 |

OTHER PUBLICATIONS

*Computer Assited Modeling* Nat'l. Academy Press Washington, D.C. (1987) 1–17, 69–105, 144–150, no month.
Cram, D. J. "The Design of Molecular Hosts, Guests and Their Complexes (Nobel Lecture)" Angew. Chem. Int. Ed. Engl., 27:1009(1988), no month.
Goodman et al., "An Unbounded Systematic Search of Conformation Space", J. Computational Chemistry, 12:1110–1117 (1991), no month.
Iimori et al., "Enantioselective Complexation with a Conformationally Homogeneous C$_2$ Podand Ionophore", Tetrahedron Letters, 30:6947–6950 (1989) no month.
Jorgensen et al., "The OPLS Potential Functions for Proteins. Energy Minimizations for Crystals of Cyclic Peptides and Crambin", Am. Chem. Soc., 110:1657–1666, (1988) no month.
Jorgensen, W. L., "Free Energy Calculations: A Breakthrough for Modeling Organic Chemistry in Solution", Acc. Chem. Res., 22:184–189, (1989), no month.
Peacock et al., "Host–Guest Complexation, 13. High Chiral Recognition of Amino Esters by Dilocular Hosts Containing Extended Steric Barriers", J. Am. Chem. Soc., 100:8190–9202, (1978) no month.
Li et al., "Podand Sulfones. Enantioselective Receptors for Peptidic Ammonium Ions", J. Am. Chem. Soc. 56:6964–6966 (1991), no month.
Still et al., "Semianalytical Treatment of Solvation for Molecular Mechanics and Dynamics", J. Am. Chem. Soc. 112:6127–6129 (1990) with Appendix, no month.

*Primary Examiner*—Edward R. Cosimano
*Attorney, Agent, or Firm*—Brumbaugh, Graves, Donohue & Raymond

[57] ABSTRACT

The effective Born radii of atoms in a molecule are determined using a new molecular modeling technique. In this approach, the electrical polarization component of solvation energy of an atom i is approximated as the electrical polarization energy given by the classical Born equation (Eq. 2), assuming that the Born radius $\alpha$ is equal to the van der Waals radius of the atom, minus the effects of all surrounding atoms, j, which displace solvent from around atom i. This displacement effect increases with the volume of the atom j and decreases as the fourth power of the separation between atom i and atom j. $E_{pol}$ for atom i can therefore be calculated using the following equation:

$$E_{pol,i} = -166(1-1/\epsilon)q_i[1/(P_0+R_i) - \Sigma PV_j/r_{ij}^4]$$

wherein $R_i$ is the van der Waals radius of atom i, $V_j$ is the volume of an atom j, and $P_0$ and $P$ are empirically determined, solvent-dependant constants or functions of $r_{ij}$. This value of $E_{pol,i}$ is then substituted into a rearranged form of the Born equation $$\alpha_i = -166(1-1/\epsilon)q_i^2/E_{pol,i}$$

to give the effective Born radius for atom i, $\alpha_i$, for use in the generalized Born equation.

4 Claims, 5 Drawing Sheets

METHOD AND APPARATUS FOR DESIGNING MOLECULAR STRUCTURES USING AN ANALYTICAL SOLUTION FOR EFFECTIVE BORN RADII

BACKGROUND OF THE INVENTION

This invention relates to the field of molecular modeling, and more specifically to the design of molecular structures to achieve particular interactions with other molecules such as biological receptors and/or substrates.

Molecular design and modeling have been carried out by a variety of approaches, including conformational searching, energy minimization, energy calculation, normal mode analysis, molecular dynamics, stochastic dynamics and Monte Carlo simulations. These approaches all generally involve the estimation of one or more energy values for a molecule being modeled, and the prediction based upon this energy value of the physical properties and structure of the molecule. See, "Computer Assisted Modeling", National Academy Press, (1987). Different energy values will be incorporated into the model depending on their importance to the molecular properties of interest. Furthermore, more sophisticated models incorporate more energy values, while simpler models incorporate fewer energy values. The success of a particular modeling effort depends on the extent to which the energy values selected accurately and completely reflect a real molecule.

In modeling the behavior of molecules in solution, one important energy value is the solvation energy, $E_{solvation}$. $E_{solvation}$ is generally viewed as the sum of three smaller energy components: the cavitation energy, $E_{cav}$, the dispersion energy, $E_{vdW}$, and the electrical polarization component of the solvation energy, $E_{pol}$. The first two components are given by the summation across the atoms in the molecule of the atomic solvation parameter, $\sigma$, times the solvent accessible surface area of the atom, A, according to the equation $$E_{cav} + E_{vdW} = \Sigma \sigma_i A_i \qquad \text{(Eq. 1)}$$

Still et al., J. Am. Chem. Soc., 112, 6127–6129 (1990). The determination of $E_{pol}$, however, is somewhat more difficult.

Classically, $E_{pol}$ (kcal/mole) for an electrical charge (q, in units of electron charge) at the center of a spherical particle of radius $\alpha$ (Å) surrounded by a medium of dielectric $\epsilon$ is given by the Born equation:

$$E_{pol} = -166(1 - 1/\epsilon)q^2/\alpha \qquad \text{(Eq. 2)}$$

M. Born, Z Physic, 1, 45 (1920). If the molecule being modeled is approximately spherical, and the charge is localized in the center of the molecule, the Born equation can be used to provide a reasonable value for $E_{pol}$. Most molecules of interest do not fit these constraints, however. Because of this, a generalized Born equation has been developed to provide a value for $E_{pol}$ as follows:

$$E_{pol} = -166(1-1/\epsilon)\Sigma_i\Sigma_j q_i q_j/(r_{ij}^2 + \alpha_{ij}e^{**}(-r_{ij}^2/4\alpha_{ij}^2))^{0.5} \qquad \text{(Eq. 3)}$$

in which $r_{ij}$ is the separation between atoms i and j and $\alpha_{ij}$ is the mean Born radius of the atom i j pair. This equation provides a value for $E_{pol}$ provided that the effective Born radii $\alpha$ of each atom in the molecule is known so that $\alpha_{ij}$ can be calculated (e.g. $\alpha_{ij} = (\alpha_i \alpha_j)^{0.5}$).

In the past, determination of the effective Born radius has been done, at best, using a semi-analytical approach such as that described in Still et al. J. Amer. Chem Soc. 112, 6127–6129 (1990), and the appendices thereto. This approach summed the Born electrostatic energies of a series of concentric shells of dielectric having thickness T beginning at the surface of atom being evaluated and extending outward to the van der Waals surface of the molecule. While this method is effective and has been incorporated in commercially available software for molecular modeling (MacroModel V 3.0), the calculation of effective Born radius for each atom is time consuming and limits the use of the approach to molecules of at most moderate size and complexity.

It is an object of the present invention to provide a more facile method of determining the effective Born radii of atoms in a complex molecular structure.

It is a further object of this invention to provide apparatus and methods which utilize the effective Born radii determined in accordance with the invention to predict the properties of molecular species.

SUMMARY OF THE INVENTION

In accordance with the invention, molecular modeling techniques can be improved and their speed increased by a new analytical approach to the determination of the effective Born radii of atoms in a molecule. In this approach, the electrical polarization component of solvation energy of an atom i is approximated as the electrical polarization energy given by the classical Born equation (Eq. 2), assuming that the Born radius $\alpha$ is equal to the van der Waals radius of the atom, minus the effects of all surrounding atoms, j, which displace solvent from around atom i. This displacement effect increases with the volume of the atom j and decreases as the fourth power of the separation between atom i and atom j. $E_{pol}$ for atom i can therefore be calculated using the following equation:

$$E_{pol,i} = -166(1 - 1/\epsilon)q_i[1/(P_0 + R_i) - \Sigma P V_j/r_{ij}^4] \qquad \text{(Eq. 4)}$$

wherein $R_i$ is the van der Waals radius of atom i, $V_j$ is the volume of an atom j, and $P_0$ and $P$ are empirically determined, solvent-dependant constants or functions of $r_{ij}$. This value of $E_{pol,i}$ is then substituted into a rearranged form of the Born equation $$\alpha_i = -166(1 - 1/\epsilon)q_i^2/E_{pol,i} \qquad \text{(Eq. 5)}$$

to give the effective Born radius for atom i, $\alpha_i$, for use in the generalized Born equation. (Eq. 3).

This calculation of effective Born radius, like most calculations involved in molecular modeling is most effectively performed using a data processing apparatus. A data processing apparatus according to the invention for accomplishing this purpose comprises (a) a data processor for performing a molecular modeling calculation, (b) input means for communicating a molecular structure to be evaluated to the data processor, (c) a storage device having stored thereon commands interpretable by the data processor effective to cause the data processor to determine effective Born radii for each atom in the molecule in accordance with the procedure outlined above, and (d) output means for communicating the results of the molecular modeling calculation performed by the data processor to the user. The effective Born radii are then used to determine the electrical polarization solvation energy for the molecule using the generalized Born equation, and this energy is combined with other energy components in accordance with the model being employed to yield a predictor of the properties of the molecule which is output from the apparatus to the user.

DETAILED DESCRIPTION OF THE INVENTION

Molecular modeling is used to evaluate potential interesting chemical structures, prior to their synthesis, to evaluate the likelihood that they will have the properties which the designer desires. Molecular modeling is particularly applicable in connection with the development of pharmaceuticals and biomimetic molecules which are intended to interact specifically with a receptor or substrate because of the complexity of the molecules (and thus of the synthesis).

A molecular designer working towards, e.g., a new pharmaceutical, will first identify one or more candidate structures to be modeled. The primary structure of these candidates, i.e., the atom-to-atom bonds, are used to construct 3-dimensional models of the molecules having standard bond lengths and angles, and thus to determine the distances between atoms in the molecule in one of its conformations. This information, combined with known values for the van der Waals radius and the volume of atoms of various types, (radii comes from standard molecular mechanics force fields (e.g. J. Am. Chem. Soc., 1657 (1988)). The volume can be calculated from $4/3\pi$ radius$^3$ and may or may not be modified for any overlapping atoms) are then utilized to calculate the effective Born radius for each atom using the method of the invention.

Figure 2:
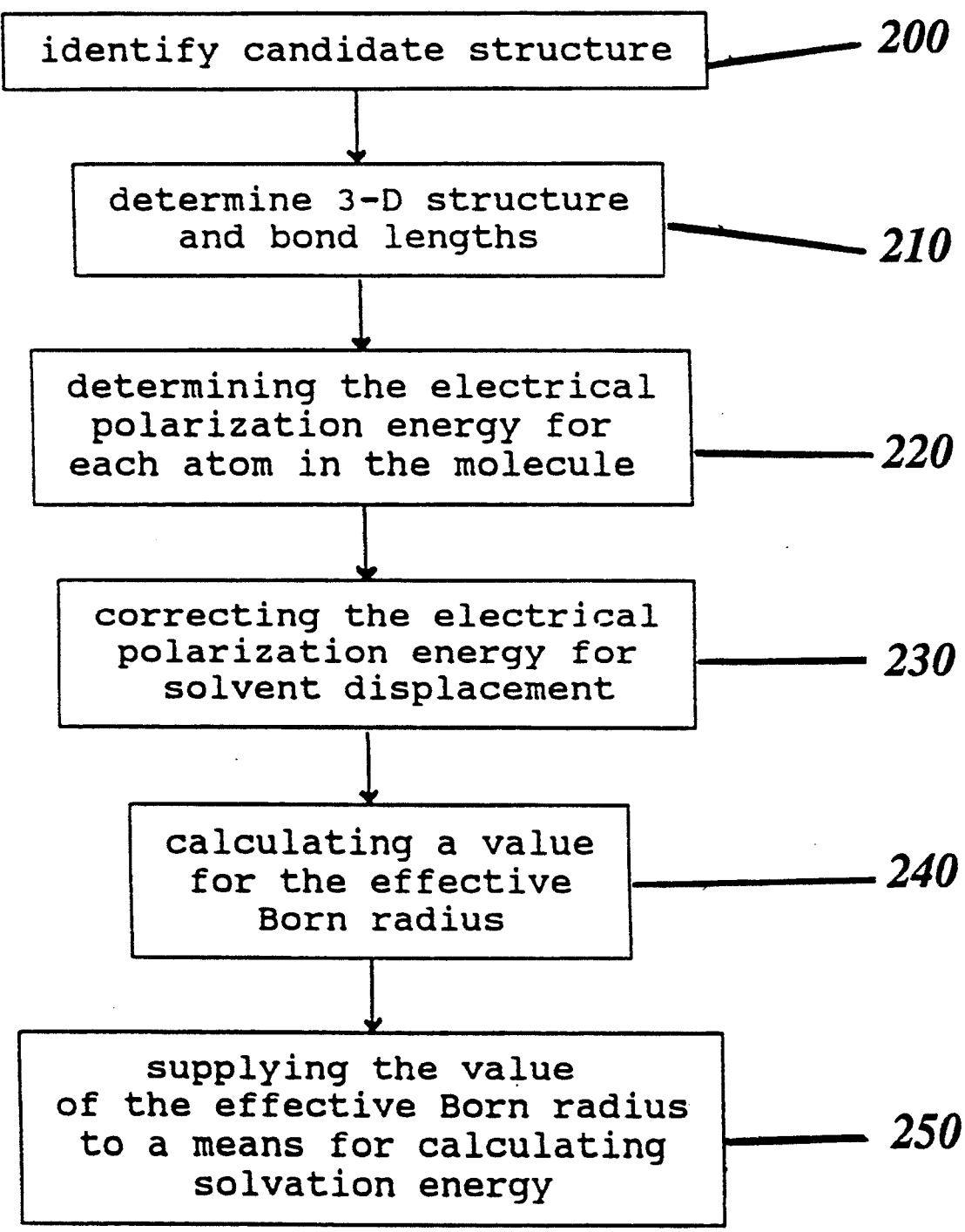
FIG. 2 shows the method of calculating the Born radii in flowchart form.

Basically, as shown in FIG. 2, the method of the invention involves identifying the candidate molecular structure (200), determining the 3-dimensional structure and bond lengths (210) determining the electrical polarization component of the solvation energy for each atom (220) using the Born equation (Eq. 2), assuming it was an isolated atom and subtracting out the solvent displacement effect of each of the other atoms in the molecule (230). This can be accomplished using the formula:

$$E_{pol,i} = -166(1-1/\epsilon)q_i [1/(P_0+R_i) - \Sigma PV_j/r_{ij}^4]  \quad (Eq. 4)$$

In the practical application of Eq. 4, however, the best results are obtained when the summation is expanded over different classifications of atoms, e.g., as shown in Eq. 6:

$$\Sigma PV_j/r_{ij}^4 = \Sigma_1 P_1 V_k/r_{ik}^4 + \Sigma_2 P_2 V_l/r_{il}^4 + \Sigma_3 P_3 V_m/r_{im}^4 \quad (Eq. 6)$$

In Eq. 6, $\Sigma_1$ is the summation over atoms k which are bonded directly to atom i by covalent chemical bonds. $\Sigma_2$ is the summation over atoms l which are bonded indirectly to atom i with one intervening atom. $\Sigma_3$ sums over all other atoms (not i, k, l). It will be understood, however, that expansion of the summation to three terms is not critical, and that more or fewer terms could be employed if desired.

In equations 4 and 6, the terms $P_0$, $P$, $P_1$, $P_2$, and $P_3$ are empirically determined constants or functions of $r_{ij}$ that depend in value on the solvent system. They are determined by computing $E_{pol,i}$ numerically for each atom in a plurality of molecules in a given solvent, using simple molecules for which the numerical approach is reasonable (See Still et al., J. Am. Chem. Soc. 112., 6127–6129 (1990)), or by determining experimental values for $E_{pol,i}$ and then optimizing the various P values to give the best fit between these values of $E_{pol,i}$ and values of $E_{pol,i}$ determined in accordance with equations 4 and 6. In this way, parameters for water as a solvent have been determined as follows:

$$P_0 = 0.2 P_1 = 1.1 P_2 = 6.9 P_3 = 35.1$$

For chloroform, the following parameters were obtained:

$$P_0 = 0.5 P_1 = 0.9 P_2 = 6.8 P_3 = 18.1$$

It will be appreciated, that the precise set of parameters obtained will depend on the molecules chosen to use in the optimization process, such that some variability in the parameters even for a particular solvent is possible.

Using the results for $E_{pol,i}$ determined for each atom in the molecule, values of $\alpha_i(240)$, are then determined and used in the generalized Born equation to determine a molecular $E_{pol}$. This, in turn, is combined with the other energy parameters, such as $E_{steric}$ and $E_{cav}$ and $E_{vdw}$ to obtain a value for $E_{total}(250)$ which can be used in molecular modeling calculations to provide meaningful predictions of the behavior of complex molecules in solution.

Figure 3:
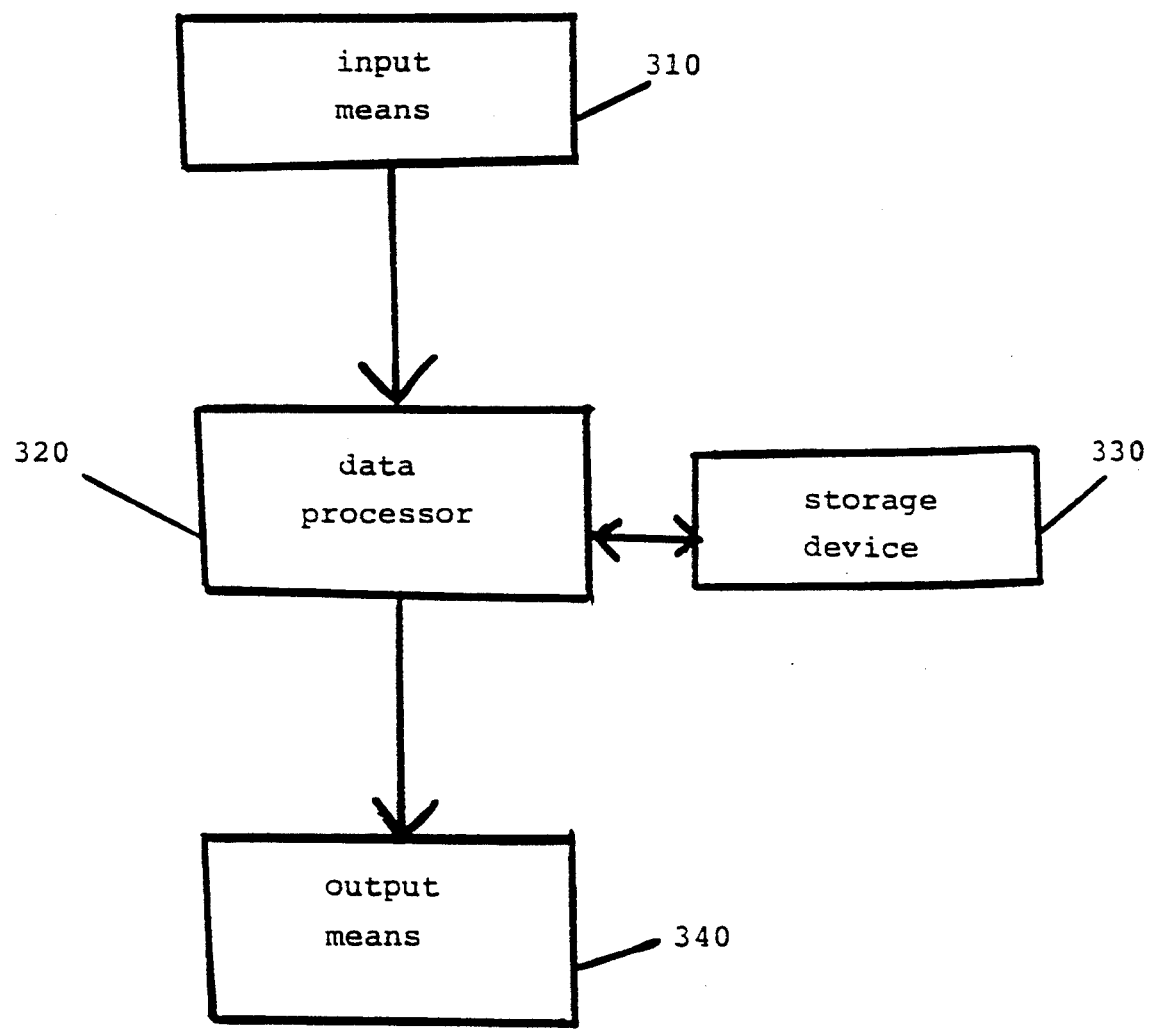
FIG. 3 shows an apparatus for use in molecular modeling in accordance with the invention in schematic form.

The method described above is advantageously carried out on an apparatus shown in FIG. 3 comprising a data processor (320) for performing a molecular modeling calculation, input means (310) for communicating a molecular structure to be evaluated and a solvent to the data processor, a storage device (330) having stored thereon commands interpretable by the data processor effective to cause the data processor to determine effective Born radii for each atom in the molecular structure by determining the electrical polarization component of the solvation energy of each atom, assuming that the Born radius of the atom was equal to its van der Waals radius, and then subtracting the solvent displacement effect of each of the other atoms in the molecule, and output means (340) for communicating the results of the molecular modeling calculation performed by the data processor to the user.

Suitable data processor's for use in an apparatus according to the invention include workstations, main frame computers and supercomputers.

Suitable input means include keyboard entry of molecular structures and solvent data, special graphically driven interface programs which use pre-defined icons to create a structural image of the molecule, atomic coordinate files from external sources such as crystallographic data bases.

Suitable storage devices include magnetic storage media such as diskettes, fixed (hard) disks and magnetic tape. Bubble memory, and various forms of read-only memory, may also be employed. Compact disk storage devices (CD-ROM) may also be used.

Suitable output devices include screen displays, printed output, and output to magnetic media or other accessible storage formats.

EXAMPLE

Figure 1:
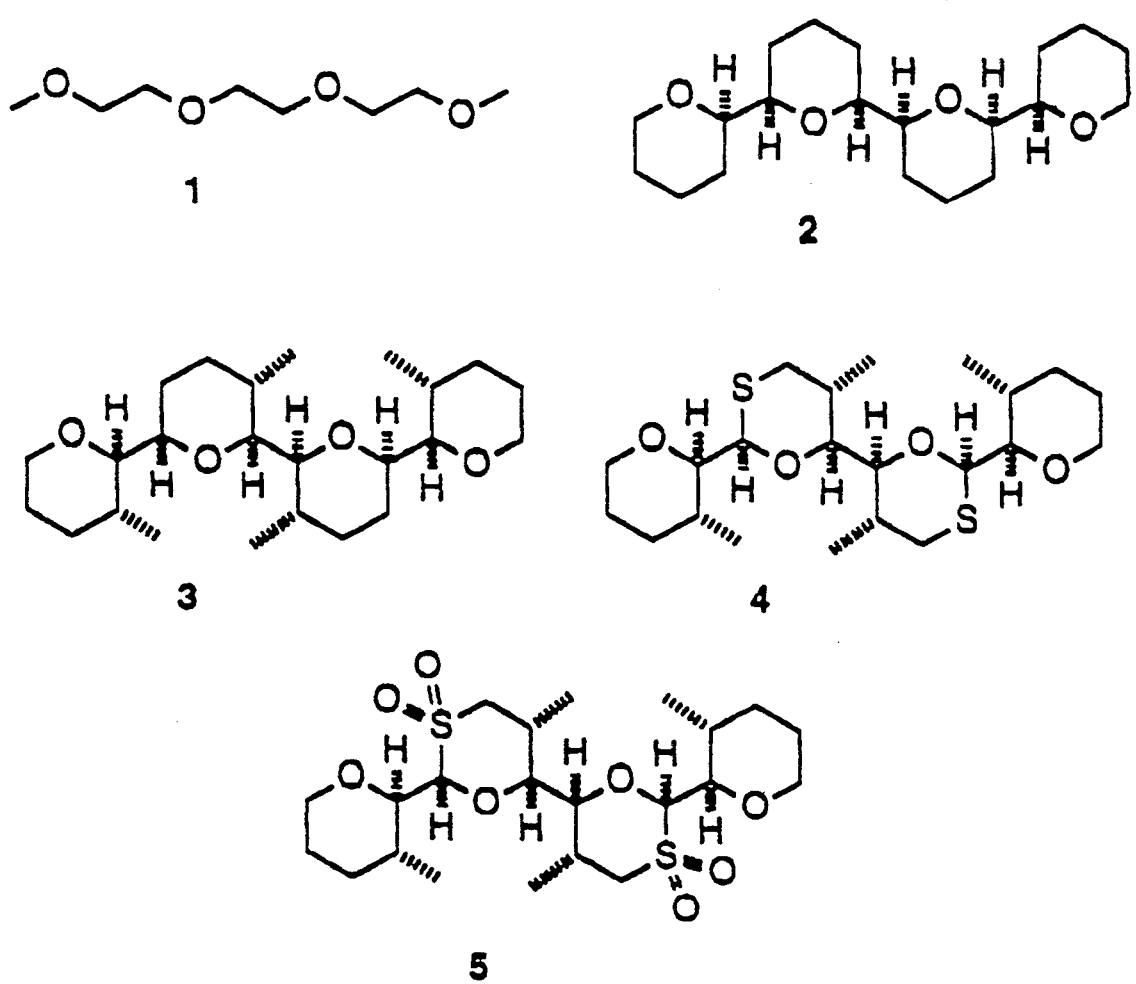
FIG. 1 shows five candidate structures which were evaluated for selective binding to L-amino acids using the method of the invention.

The method of the invention was used to screen candidate molecules prior to synthesis in a project directed toward the creation of new molecules that would selectively bind only the natural (L) form of amino acid derivatives. Five molecular structures shown in FIG. 1 were originally considered as candidates.

To evaluate the ability of these molecules to interact selectively with L-amino acids, the procedures for evaluating $a_i$ in Macro Model were replaced with a procedure in accordance with the invention. The source code for this procedure, written in Fortran, is attached as Appendix I. This modified program was loaded onto the hard disk of a Silicon Graphics UNIX workstation. Structures were input by manual drawing with a mouse provided with the workstation.

Using manually drawn input structure, a conformational search (Goodman et al., J. Computational Chem., 12, 1110 (1991)) was carried out on each of the candidate molecules using our solvation energies ($E_{solvation}$) to establish which of the molecules had shapes in solution having open binding sites similar to those of molecules such a crown ethers which bind amino acid salts. This was done by visual inspection of structures on computer display. (See, D. J. Cram, Angew Chem. Int. Ed, 27, 1009 (1988) and J. Am. Chem. Soc., 188, 8190 (1978)).

As a result of this analysis, candidate molecules 1 and 2 were predicted to exist in a plurality of low energy forms. Such a plurality of forms is associated with poor association properties according to the principle of preorganization. Thus, molecules 1 and 2 were rejected. On the other hand, molecules 3, 4, and 5 were predicted to have primarily one low energy form and were therefore given further consideration.

The next phase of the analysis was to dock amino acids into the low energy forms of each of the remaining candidates and carry out energy minimizations. (Brukert & Allison, "Molecular Mechanics", ACS Washington D.C. (1977)). Compounds 3 and 5 were predicted to have the lowest energy when combined with amino acids, as compared to the free molecules. Candidate molecule 4 was therefore eliminated.

Finally, free energy perturbation was used with our solvation energies to calculate the free energy difference between an L amino acid and a D-amino acid binding to candidate molecules 3 and 5. W. L. Jorgensen, Accnts. Chem. Res., 22, 184 (1989). This showed that candidate molecule 5 was predicted to have a larger free energy difference between complexes with L- and D-amino acids. Thus, candidate molecule 5 was predicted to be the most selective receptor for L-amino acids of the five candidate molecules considered.

Figure 4:
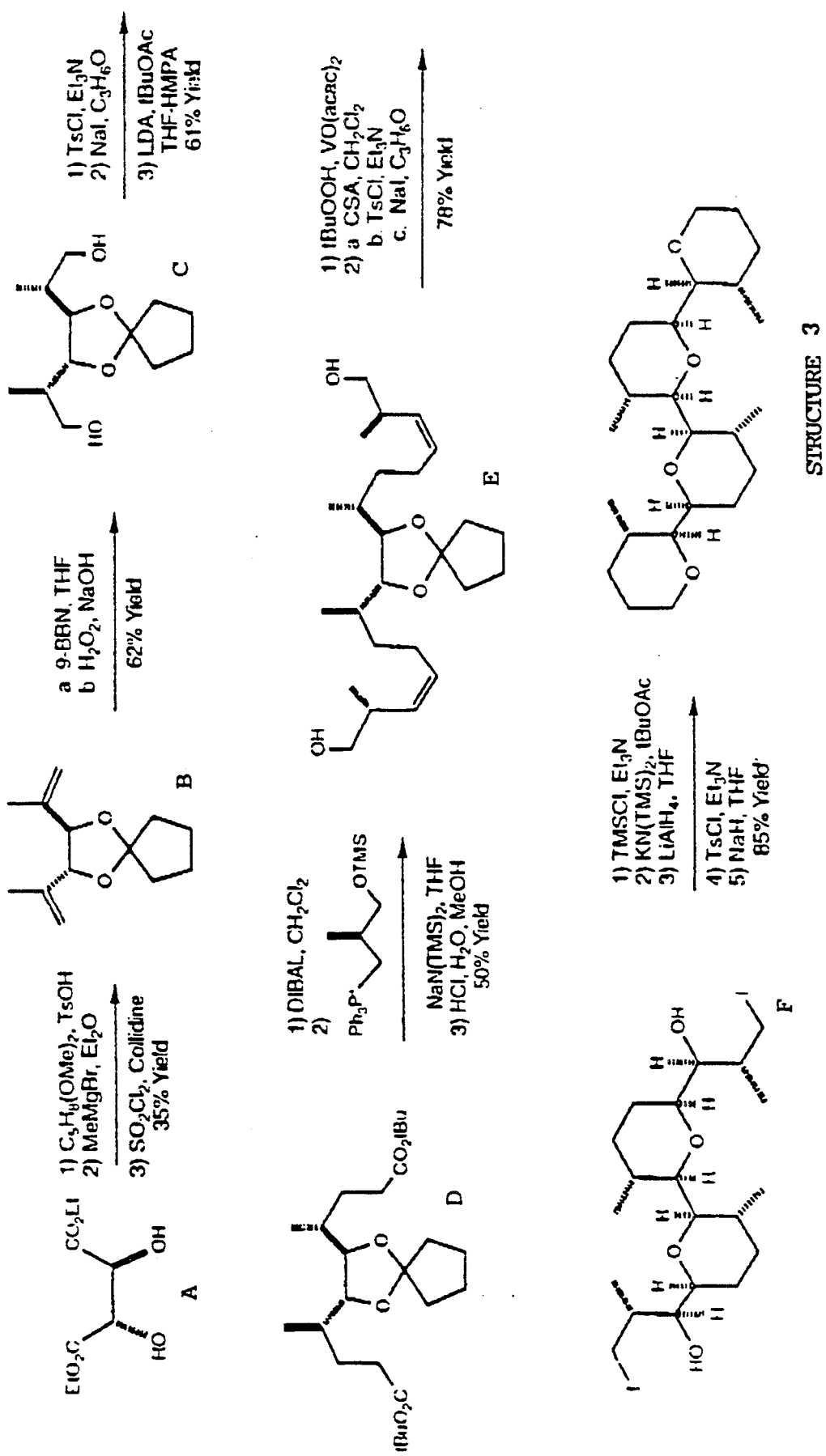
FIG. 4 shows the steps for synthesizing candidate structure 3 in FIG. 1.

Molecules of structures 3 and 5 were synthesized as described in Timosi et al., Tetrahedron Lett., 30, 6947 (1989) and Li et al. J. Org. Chem. 56 6984–966 (1991) and evaluated to test this prediction. The synthesis of structure 3 is shown in FIG. 4. Diethyl tartrate (A) was converted to its cyclopentylidene ketal using 1,1-dimethoxycyclopentane and catalytic acid. Next, excess methyl magnesium bromide was added to convert both esters to the corresponding tertiary alcohols which were then dehydrated using thionyl chloride to give diene B. This diene was hydroborated using 9-borabicyclononane (9-BBN) and then worked up with alkaline peroxide to produce C. Next, the primary alcohols were tosylated, displaced by sodium iodide in acetone and then used to alkylate the enolate of t-butyl acetate in tetrahydrofuran giving D. After reducing the esters to aldehydes using diisobutylaluminum hydride (DIBAL), Wittig reaction with the chiral reagent shown followed by silyl ether hydrolysis gave E. This molecule was epoxidized using t-butyl hydroperoxide and cyclized with camphor sulfonic acid (CSA). The primary alcohols were then converted to iodides using toluene-sulfonyl chloride and then sodium iodide yielding F. The secondary alcohols were protected using trimethylsilyl ether blocking groups. The iodide substituents were displaced using the lithium enolate of t-butyl acetate, and the resulting diester reduced with lithium aluminum hydride resulting in primary alcohols which were then tosylated. Finally, sodium hydride was used to close the outer six-membered rings by Williamson ether synthesis to give structure 3.

Figure 5:
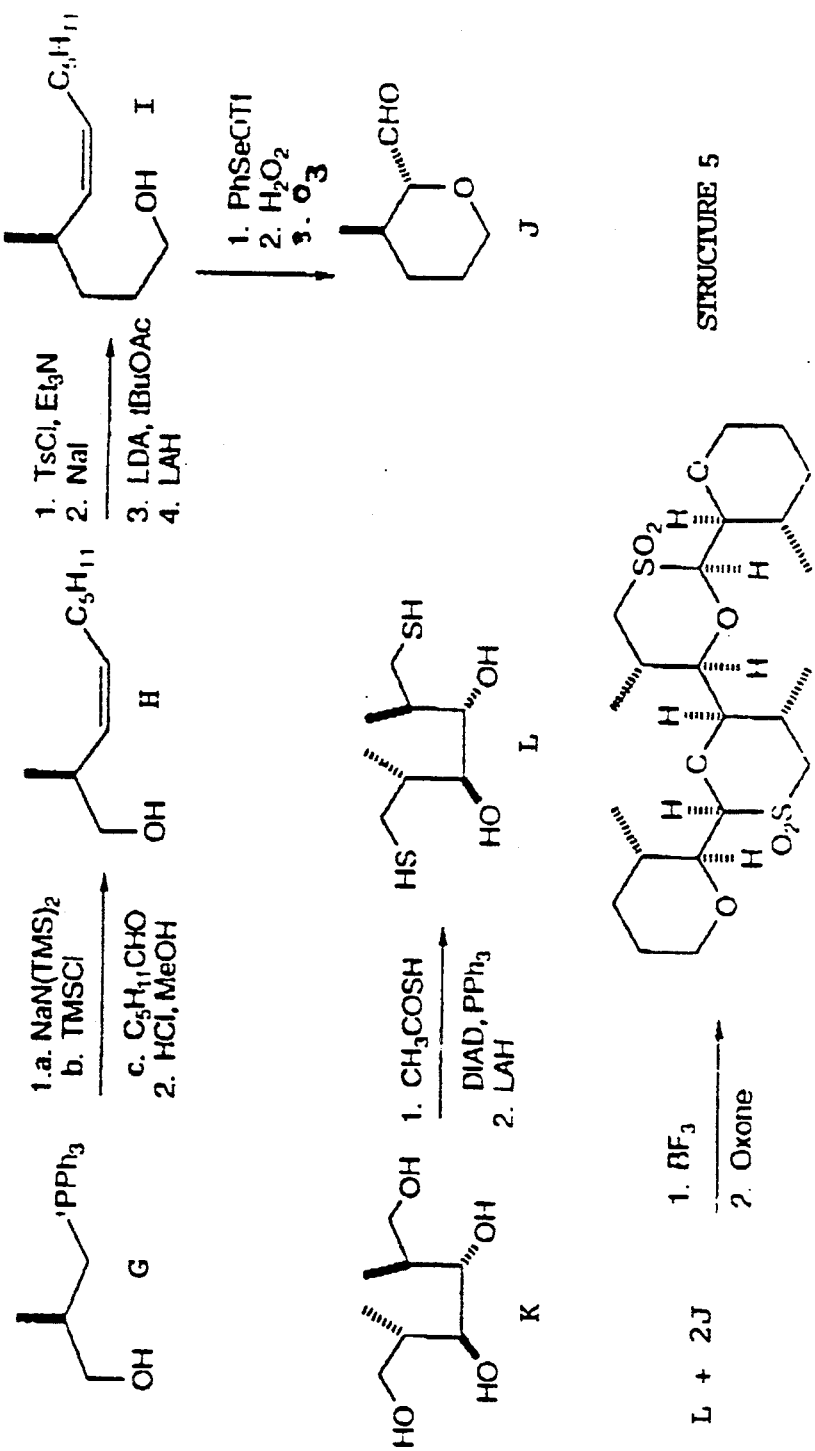
FIG. 5 shows the steps for synthesizing candidate structure 5 in FIG. 1.

The synthesis of structure 5 is shown in FIG. 5. The Wittig reagent from sodium hexamethyldisilazide and phosphonium ion G was silylated using one equivalent of trimethylsilyl chloride and then treated with hexanal. After hydrolysis of the resulting olefinic silyl ether, olefinic alcohol H was obtained. That molecule was tosylated using toluenesulfonyl chloride and then treated with sodium iodide to produce the corresponding primary iodide. Alkylation of that material using the lithium enolate of t-butyl acetate in tetrahydrofuran followed by lithium aluminum hydride reduction then gave I. Compound I was cyclized using phenyl selenenyl triflate and then eliminated as the selenoxide using hydrogen peroxide. Finally, ozonolysis gave aldehyde J. Compound K was prepared by mild acid hydrolysis of the hydroboration product of compound B (shown in FIG. 4). This compound was treated under Mitsunobu conditions with thioacetic acid and then reduced with lithium aluminum hydride to compound L. Compounds J and L were mixed in a 2:1 ratio and treated with boron trifluoride etherate to provide a tetracylic S,O-acetal. This acetal was oxidized using oxone to the corresponding sulfone thereby producing structure 5. As shown in Table 1, while both structures exhibited some measure of selectivity (enantiomeric excess>0), the model correctly predicted the superiority of structure 5.

TABLE 1

| Amino Acid Derivative | Measures Enantioselectivity (% Enantiomeric Excess) | |
|---|---|---|
|  | Structure 3 | Structure 5 |
| $^+NH_3$—Phe—$CO_2Me$ | 36% | 60% |
| $^+NH_3$—Phe—CONHMe | 31% | 52% |
| $^+NH_2$Pro—$CO_2Me$ | <10% | 78% |
| $^+NH_2$Pro—CONHMe | <10% | 80% |
| $^+NH_3$—Pla—$CO_2Me$ | 40% | 55% |

I claim:

1. An apparatus for use in molecular modeling comprising:
   (a) a data processor for performing a molecular modeling calculation,
   (b) input means for communicating a molecular structure to be evaluated and a solvent to the data processor,
   (c) a storage device having stored thereon commands which cause the data processor to
      (1) assume the Born radius of each atom of the molecular structure is equal to the van der Waals radius of said atom
      (2) calculate the solvent displacement effect of each of the other atoms of the molecular structure in said solvent for each atom of the molecular structure
      (3) calculate the electrical polarization component of the solvation energy, $E_{pol}$ for each atom i of the molecular structure, in accordance with the equation $$E_{pol,i} = -166(1 - 1/\epsilon)q_i[1/(P_0 + R_i) - \Sigma P V_j/r_{ij}^4]$$

wherein $\epsilon$ is the dielectric constant of the solvent, $R_i$ is the van der Waals radius of atom i, $V_j$ is the volume of an atom j of the molecular structure, different from atom i, $r_{ij}$ is the separation between atoms i and j, and $P_0$ and P are empirically determined, solvent-dependent parameters
      (4) calculate the effective Born radius for each atom of the molecular structure by substituting the calculated electrical polarization component of the solvation energy in said solvent for each atom of the molecular structure into the Born equation, and
   (d) output means for communicating the effective Born radius for each atom of the molecular structure to be evaluated calculated by the data processor to a user.

2. An apparatus for use in molecular modeling comprising:
   (a) a data processor for performing a molecular modeling calculation,
   (b) input means for communicating a molecular structure to be evaluated and a solvent to the data processor,
   (c) a storage device having stored thereon commands which cause the data processor to
      (1) assume the Born radius of each atom of the molecular structure is equal to the van der Waals radius of said atom
      (2) calculate the solvent displacement effect of each of the other atoms of the molecular structure in said solvent for each atom of the molecular structure
      (3) calculate the electrical polarization energy $$E_{pol,i} = -166(1 - 1/\epsilon)q_i[1/(P_0 + R_i) - \{\Sigma_1 P_1 V_k/r_{ik}^4 + \Sigma_2 P_2 V_l/r_{il}^4 + \Sigma_3 P_3 V_m/r_{im}^4\}]$$

wherein $\epsilon$ is the dielectric constant of the solvent, $R_i$ is the van der Waals radius of atom i, $\Sigma_1$ is a summation over atoms k of the molecular structure which are bonded directly to atom i by chemical bonds, $\Sigma_2$ is a summation over atoms l of the molecular structure which are bonded indirectly to atom i with one intervening atom, $\Sigma_3$ is a summation over all other atoms in the molecule, $V_x$ is the volume of an atom x of the molecular structure different from atom i, $r_{ix}$ is the separation between atoms i and x, and $P_0$, $P_1$, $P_2$, and $P_3$ are empirically determined, solvent-dependent parameters or functions of $r_{ix}$
      (4) calculate the effective Born radius for each atom of the molecular structure by substituting the calculated electrical polarization component of the solvation energy in said solvent for each atom of the molecular structure into the Born equation, and
   (d) output means for communicating the effective Born radius for each atom of the molecular structure to be evaluated calculated by the data processor.

3. A method for screening a molecule for suitability for a particular purpose comprising the steps of:
   (a) selecting one or more candidate molecules and a solvent,
   (b) inputting the three-dimensional structure of the candidate molecule and solvent-based information into an apparatus for performing molecular modeling calculations,
   (c) using the apparatus to calculate the effective Born radius of each atom of the candidate molecule, wherein the apparatus assumes the Born radius of each atom of the candidate molecule is equal to the van der Waals radius of said atom, calculates the solvent displacement effect of each of the other atoms of the candidate molecule in said solvent for each atom of the candidate molecule, and determines the electrical polarization component $E_{pol}$ of the solvation energy in said solvent for each atom i of the candidate molecule in accordance with the equation $$E_{pol,i} = -166(1 - 1/\epsilon)q_i[1/(P_0 + R_i) - \Sigma P V_j/r_{ij}^4]$$

wherein $\epsilon$ is the dielectric constant of the solvent, $R_i$ is the van der Waals radius of atom i, $V_j$ is the volume of an atom j of the candidate molecule, different from atom i, $r_{ij}$ is the separation between atoms i and j, and $P_0$ and P are empirically determined, solvent-dependent parameters or functions of $R_{ij}$
and wherein the apparatus determines the effective Born radius by substituting the determined electrical polarization component into the Born equation,
   (d) substituting the effective Born radius in a generalized Born equation to determine an electrical polarization energy component of the solvation energy in said solvent of the candidate molecule,
   (e) combining the electrical polarization energy component calculated in (d) with the cavitation energy of the candidate molecule and the dispersion energy of the candidate molecule to obtain the total solvation energy of the candidate molecule,
   (f) predicting the physical properties of the candidate molecule from the total solvation energy of the candidate molecule,
   (g) evaluating the suitability of the candidate molecule for a particular purpose from the predicted physical properties of the candidate molecule, and
   (h) synthesizing the candidate compound.

4. A method for screening a molecule for suitability for a particular purpose comprising the steps of:
   (a) selecting one or more candidate molecules and a solvent, (b) inputting the three-dimensional structure of the candidate molecule and solvent-based information into an apparatus for performing molecular modeling calculations, (c) using the apparatus to calculate the effective Born radius of each atom of the candidate molecule, wherein the apparatus assumes the Born radius of each atom of the candidate molecule is equal to the van der Waals radius of said atom, calculates the solvent displacement effect of each of the other atoms of the candidate molecule in said solvent for each atom of the candidate molecule, determines the electrical polarization component $E_{pol}$ of the solvation energy in said solvent for each atom i of the candidate molecule in accordance with the equation $$E_{pol,i} = -166(1-1/\epsilon)q_i[1/(P_0+R_i) - \{\Sigma_1 P_1 V_k/r_{ik}^4 + \Sigma_2 P_2 V_l/r_{il}^4 + \Sigma_3 P_3 V_m/r_{im}^4\}]$$

wherein $\epsilon$ is the dielectric constant of the solvent, $R_i$ is the van der Waals radius of atom i, $\Sigma_1$ is a summation over atoms k of the candidate molecule which are bonded directly to atom i by chemical bonds, $\Sigma_2$ is a summation over atoms l of the candidate molecule which are bonded indirectly to atom i with one intervening atom, $\Sigma_3$ is a summation over all other atoms in the molecule, $V_x$ is the volume of an atom x of the candidate molecule different from atom i, $r_{ix}$ is the separation between atoms i and x, and $P_0$, $P_1$, $P_2$, and $P_3$ are empirically determined, solvent-dependent parameters or functions of $r_{ix}$
and wherein the apparatus determines the effective Born radius by substituting the determined electrical polarization component into the Born equation, (d) substituting the effective Born radius in a generalized Born equation to determine an electrical polarization energy component of the solvation energy in said solvent of the candidate molecule, (e) combining the electrical polarization energy component calculated in (d) with the cavitation energy of the candidate molecule and the dispersion energy of the candidate molecule to obtain the total solvation energy of the candidate molecule, (f) predicting the physical properties of the candidate molecule from the total solvation energy of the candidate molecule, (g) evaluating the suitability of the candidate molecule for a particular purpose from the predicted physical properties of the candidate molecule, and (i) synthesizing the candidate molecule.

* * * * *

UNITED STATES PATENT AND TRADEMARK OFFICE
CERTIFICATE OF CORRECTION

PATENT NO. : 5,420,805

DATED : May 30, 1995

INVENTOR(S) : Still et al.

It is certified that error appears in the above-indentified patent and that said Letters Patent is hereby corrected as shown below:

Title page, line 6 of Item 56 "Assited" should read --Assisted--

Title page, line 10 of Item 56 "1009" should read --1009-1020--

Col. 2, line 47, "solvent-dependant" should read --solvent dependent--

Col. 4, line 66 "processor's" should read --processors--

Col. 5, line 38 "such a" should read --such as--

Signed and Sealed this

Third Day of October, 1995

Attest:

BRUCE LEHMAN

Attesting Officer

Commissioner of Patents and Trademarks